(12) United States Patent
Kurita

(10) Patent No.: US 8,233,687 B2
(45) Date of Patent: Jul. 31, 2012

(54) ULTRASONIC IMAGING APPARATUS AND A METHOD OF OBTAINING ULTRASONIC IMAGES

(75) Inventor: Koichiro Kurita, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1277 days.

(21) Appl. No.: 11/868,722

(22) Filed: Oct. 8, 2007

(65) Prior Publication Data
US 2008/0089571 A1  Apr. 17, 2008

(30) Foreign Application Priority Data

Oct. 17, 2006 (JP) ................................. 2006-282665

(51) Int. Cl.
*A61B 8/06* (2006.01)
*A61B 8/08* (2006.01)
(52) U.S. Cl. ........ 382/131; 382/128; 382/132; 600/437; 600/443; 600/444; 600/445; 600/455
(58) Field of Classification Search .................. 382/128, 382/131, 132; 600/437, 443, 444, 445, 455
See application file for complete search history.

(56) References Cited

U.S. PATENT DOCUMENTS

| | | | | |
|---|---|---|---|---|
| 4,596,145 A * | 6/1986 | Smith et al. | ...................... | 73/626 |
| 5,456,255 A * | 10/1995 | Abe et al. | ...................... | 600/443 |
| 5,546,807 A * | 8/1996 | Oxaal et al. | ...................... | 73/606 |
| 5,551,434 A * | 9/1996 | Iinuma | ........................... | 600/455 |
| 5,668,648 A * | 9/1997 | Saito et al. | ........................ | 359/9 |
| 6,221,016 B1 * | 4/2001 | Hayakawa | .................... | 600/443 |
| 6,245,017 B1 * | 6/2001 | Hashimoto et al. | ........... | 600/447 |
| 6,248,074 B1 * | 6/2001 | Ohno et al. | .................... | 600/463 |
| 6,276,211 B1 * | 8/2001 | Smith | .............................. | 73/626 |
| 6,374,674 B1 * | 4/2002 | Mine | ............................... | 73/606 |
| 6,602,196 B2 * | 8/2003 | Suzuki et al. | .................. | 600/455 |
| 6,635,018 B2 * | 10/2003 | Kawagishi et al. | ........... | 600/447 |
| 6,640,633 B2 * | 11/2003 | Satoh | .............................. | 73/626 |
| 6,973,831 B2 * | 12/2005 | Satoh | .............................. | 73/618 |
| 6,979,292 B2 * | 12/2005 | Kanayama et al. | ........... | 600/437 |
| 7,110,583 B2 * | 9/2006 | Yamauchi | ..................... | 382/128 |
| 7,912,269 B2 * | 3/2011 | Ikeda et al. | .................... | 382/131 |

(Continued)

FOREIGN PATENT DOCUMENTS
JP   9-223155   8/1997
(Continued)

OTHER PUBLICATIONS

Japanese Office Action issued Dec. 20, 2011 in patent application No. 2006-282665.

*Primary Examiner* — David A Vanore
(74) *Attorney, Agent, or Firm* — Oblon, Spivak, McClelland, Maier & Neustadt, L.L.P.

(57) ABSTRACT

An ultrasonic probe and a transmitter/receiver scan a 3D region using ultrasonic beams by raising the scanning line density of the transmission of ultrasonic beams for a region of interest compared to the scanning line density of the transmission of ultrasonic beams for regions other than the region of interest among the 3D regions. An image-generating part generates ultrasonic-image data of the 3D region, based on the received beams that have been obtained by the scan.

15 Claims, 8 Drawing Sheets

U.S. PATENT DOCUMENTS 7,985,182 B2 * 7/2011 Ichioka et al. ................ 600/444

FOREIGN PATENT DOCUMENTS

| JP | 10-5219 | 1/1998 |
| --- | --- | --- |
| JP | 2000-116651 | 4/2000 |
| JP | 2000-139908 | 5/2000 |
| JP | 2001-120549 | 5/2001 |
| JP | 2003-265475 | 9/2003 |
| JP | 2004-275223 | 10/2004 |
| JP | 2005-245936 | 9/2005 |
| JP | 2006-204621 | 8/2006 |

* cited by examiner

ULTRASONIC IMAGING APPARATUS AND A METHOD OF OBTAINING ULTRASONIC IMAGES

BACKGROUND OF THE INVENTION

1. Field of the Invention

The present invention is related to an ultrasonic imaging apparatus and a method of obtaining ultrasonic images for scanning a 3D region using ultrasonic waves. In particular, the present invention is related to an ultrasonic imaging apparatus and the method of obtaining the ultrasonic images for scanning by varying the transmission/reception conditions of ultrasonic waves, depending on the region.

2. Description of the Related Art

An ultrasonic imaging apparatus scans a predetermined range with repeating transmission/reception of ultrasonic waves and generates ultrasonic images, based on data that has been obtained by the scan.

A 2D array probe comprises a plurality of ultrasonic transducers that are two-dimensionally arranged. The 2D array probe can scan a 3D region using ultrasonic beams. Image processing such as volume rendering (hereinafter, may be referred to as "VR processing") and MPR (Multi-Planar Reconstruction) processing is applied to volume data that has been obtained by scanning the 3D region, thereby generating 3D image data or image data on an arbitrary cross section.

In this ultrasonic imaging apparatus, the volume rate and image quality of an ultrasonic image have a relationship of trade-off. For example, when obtaining a high-definition ultrasonic image while enhancing the volume rate, it is necessary to scan by narrowing down the 3D scanning region. Lowering the scanning line density of ultrasonic beams by reducing the number of transmission/reception times of ultrasonic beams makes it possible to improve the volume rate. However, the image quality of the ultrasonic image obtained by the scan thereby decreases.

In addition, raising the scanning line density of ultrasonic beams by increasing the number of transmission/reception times of ultrasonic beams enables acquisition of a high-definition ultrasonic image. However, the volume rate during such a scan will decrease.

Thus, as the density of the scanning line of ultrasonic beams is higher, the image quality of the ultrasonic image obtained by the scan improves further, but the volume rate will decrease. Conversely, as the density of the scanning line of ultrasonic beams is lower, the volume rate during the scan improves further, but the image quality of the ultrasonic image obtained by the scan will decrease.

Ultrasonic imaging apparatuses according to the prior art sets a region of interest (ROI) on the ultrasonic image obtained by transmitting/receiving ultrasonic beams and limits the range to be scanned by ultrasonic beams (e.g., Japanese Patent Laid-open Publication 2005-245936).

However, ultrasonic imaging apparatuses according to the prior art usually change the scanning line density of ultrasonic beams for the entire region to be scanned and then scan the entire region in accordance with the changed scanning line density. Therefore, it has been impossible to improve the image quality of only the sites that are necessary for diagnosis among the sites represented in an ultrasonic image obtained by a scan. For example, when obtaining an ultrasonic image of the heart, it has been difficult to improve the image quality of only the heart wall, even while focusing on the heart wall of a heart. Thus, conventionally, it has been possible to adjust the image quality of the entire ultrasonic image only, while it has been difficult to partially adjust the image quality of ultrasonic images.

According to the prior art, when the scanning line density of ultrasonic beams can be changed only in the entire region to be scanned, the following problems arise. For example, when the scanning line density of ultrasonic beams is lowered in the entire region, the volume rate increases, but image quality of the site of interest will decrease. Consequently, a high-definition ultrasonic image suitable for diagnosis cannot be obtained.

In addition, when increasing the scanning line density of ultrasonic beams for the entire region, the entire image quality including the site of interest would increase, but the volume rate will decrease. Therefore, an image that is suitable for diagnosis in which real-time properties need to be ascertained cannot be obtained.

For example, when diagnosing a site in motion such as a heart, real-time properties need to be ascertained. However, when the scanning line density of ultrasonic beams is lowered in the entire region to be scanned in order to improve the volume rate, the image quality of the site of interest such as a heart wall will also decrease. Conversely, when the scanning line density of ultrasonic beams is raised in the entire region to be scanned in order to improve the image quality of the site of interest such as a heart wall, the volume rate will decrease. Consequently, an image suitable for diagnosing a site in motion such as a heart cannot be obtained.

SUMMARY OF THE INVENTION

The objective of the present invention is to provide an ultrasonic imaging apparatus, as well as a method of obtaining ultrasonic images that are capable of improving the image quality of a region while preventing a decrease in the volume rate.

The first aspect of the present invention is an ultrasonic imaging apparatus comprising a scanner for scanning—while the scanning line density of the transmission of ultrasonic beams for a region of interest among 3D regions is higher than the scanning line density of the transmission of ultrasonic beams for regions other than the region of interest among 3D regions—the 3D region using ultrasonic beams, and an image-generating part configured to generate ultrasonic-image data of the 3D region, based on the received beams that have been obtained by the scan.

In the first aspect, it becomes possible to improve the image quality of the region of interest while preventing a decrease in the volume rate by raising the scanning line density of the transmission of ultrasonic beams for a region of interest compared to the scanning line density of the transmission of ultrasonic beams for regions other than the region of interest.

In addition, the second aspect of the present invention is an ultrasonic imaging apparatus according to the first aspect, wherein the scanner scans a predetermined slice by using ultrasonic beams to scan in the main scanning direction, further scans a 3D region by scanning a plurality of slices by using ultrasonic beams to scan in a direction perpendicular to the main scanning direction, and equalizes the number of received beams to be received per slice by changing the number of transmission times of ultrasonic beams and the number of parallel signals per slice.

Moreover, the third aspect of the present invention is a method of obtaining ultrasonic images, comprising scanning—by raising the scanning line density of the transmission of ultrasonic beams for a region of interest compared to the scanning line density of ultrasonic beams for regions other than the region of interest among 3D regions—the 3D region using ultrasonic beams, and generating ultrasonic-image data of the 3D region, based on the received beams that have been obtained by the scan.

DETAILED DESCRIPTION OF THE EMBODIMENTS

Configuration

Figure 1:
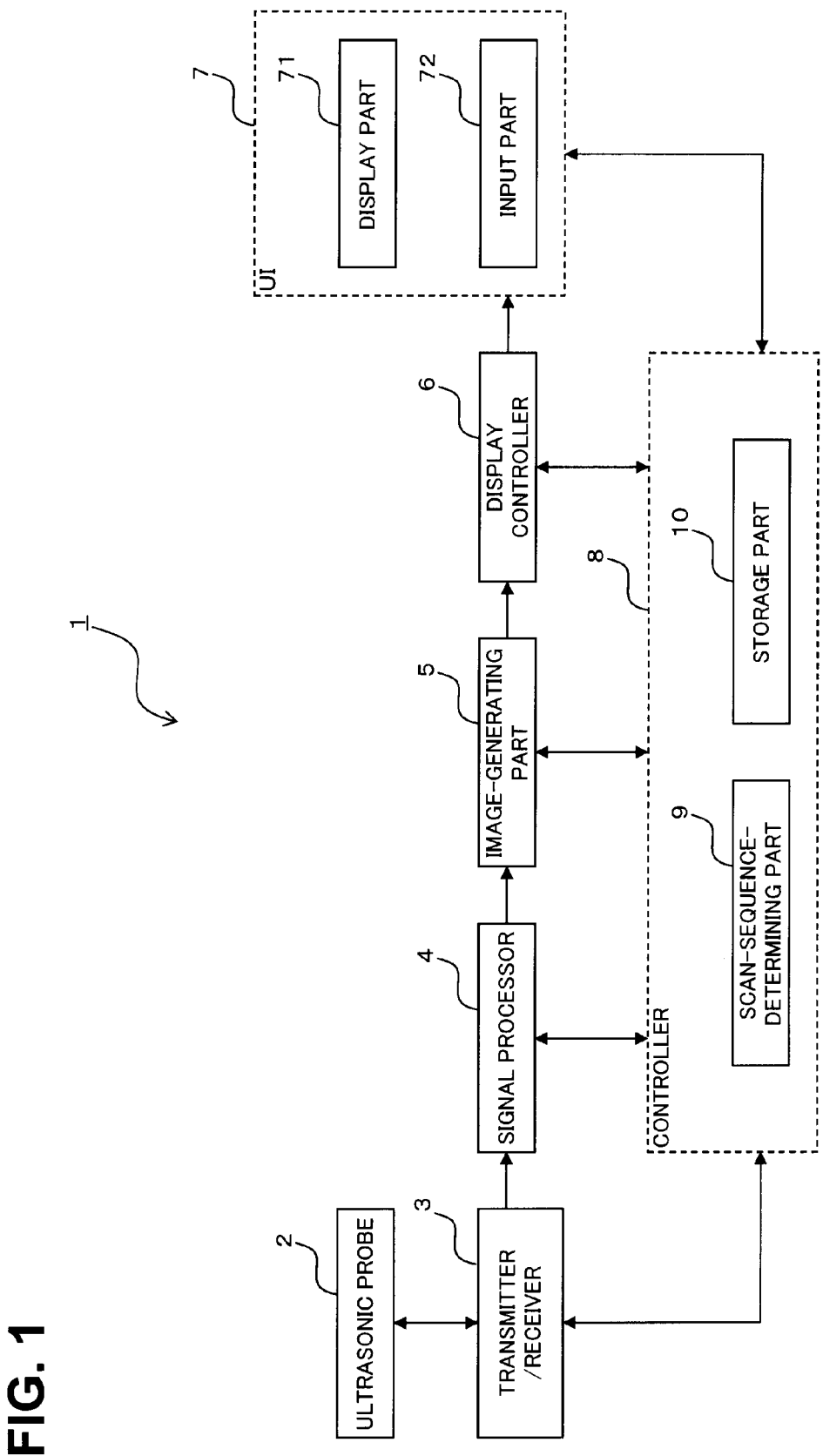
FIG. 1 is a block diagram that shows an ultrasonic imaging apparatus according to an embodiment of the present invention.
Figure 2A:
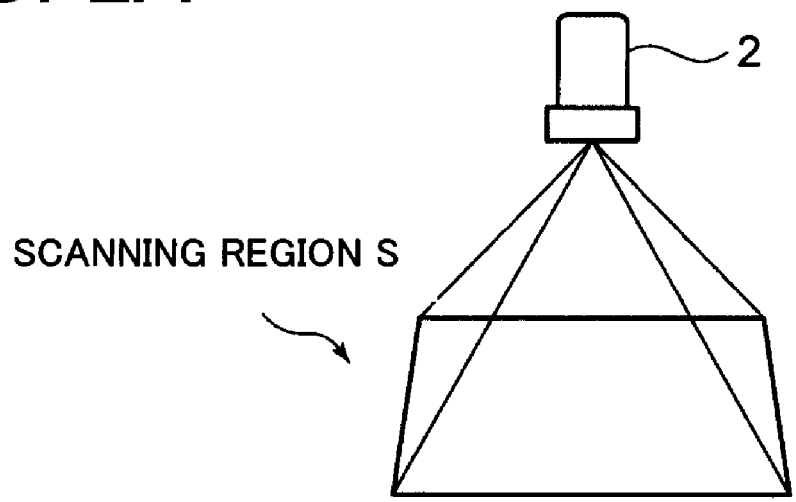
FIG. 2A is a diagram that shows a region to be scanned by a 2D array probe.
Figure 2B:
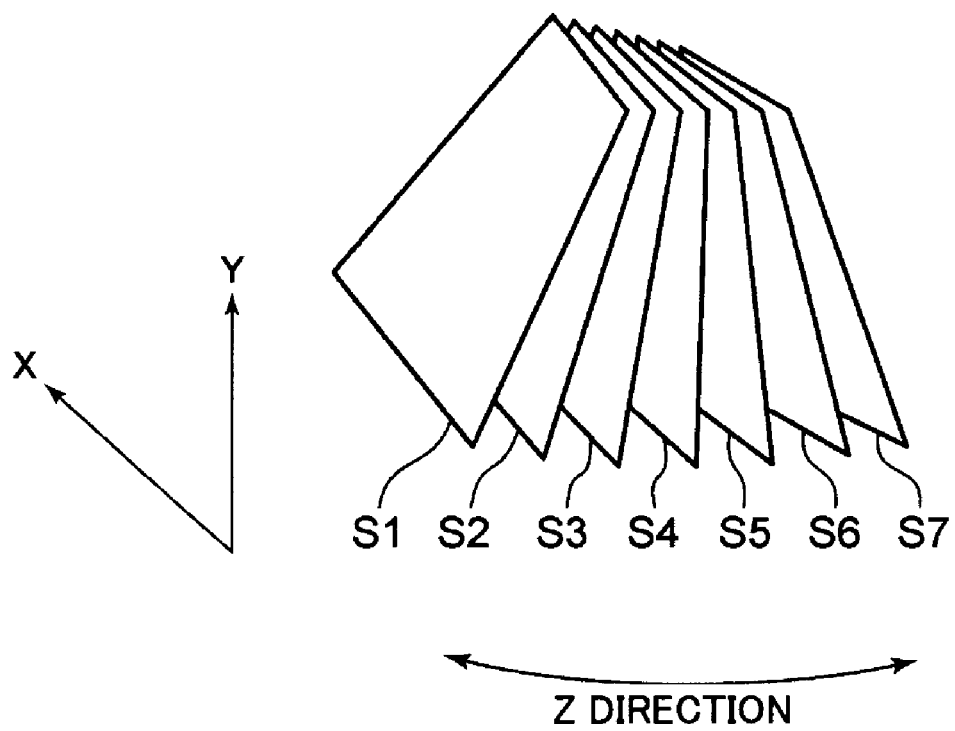
FIG. 2B is a diagram that shows a region to be scanned by a 2D array probe.

An ultrasonic imaging apparatus according to an embodiment of the present invention will be explained with reference to FIGS. 1, 2A, and 2B. FIG. 1 is a block diagram that shows an ultrasonic imaging apparatus according to an embodiment of the present invention. FIGS. 2A and 2B are diagrams that show a region to be scanned by a 2D array probe.

An ultrasonic imaging apparatus 1 according to this embodiment obtains a high-definition ultrasonic image by raising the scanning line density of the transmission of ultrasonic beams for a region of interest (ROI). In addition, the ultrasonic imaging apparatus 1 improves the volume rate by performing parallel signal processing to lower the scanning line density of the transmission of ultrasonic beams for regions other than the region of interest (ROI). Thereby, a high-definition ultrasonic image is obtained in the region of interest (ROI) while preventing a decrease in the volume rate. Hereinafter, the configuration of each portion of the ultrasonic imaging apparatus 1 will be explained.

An ultrasonic probe 2 is composed of a 2D array probe. The 2D array probe has ultrasonic transducers that are two-dimensionally arranged, and receives 3D data with a shape that radially spreads as an echo signal by three-dimensionally transmitting ultrasonic beams and receiving the reflected waves. In addition, a 1D array probe may be employed as an ultrasonic probe 2 instead of the 2D array probe. For example, a 1D array probe may be employed in which the ultrasonic transducers are arranged in a predetermined direction (scanning direction) and that is capable of mechanically swinging the ultrasonic transducers in a direction perpendicular to the scanning direction.

Herein, the region to be scanned by the ultrasonic probe 2 will be explained with reference to FIGS. 2A and 2B. As shown in FIG. 2A, a scanning region S that can be scanned by the ultrasonic probe 2 is a 3D space. Specifically, as shown in FIG. 2B, the ultrasonic probe 2 scans a slice S1 that is defined by a transmission/reception direction (Y direction) and a main scanning direction (X direction) by using ultrasonic beams to scan in the main scanning direction (X direction) while transmitting the ultrasonic beams in the transmission/reception direction (Y direction). Furthermore, the ultrasonic probe 2 scans a plurality of slices S1, S2, S3, . . . by using ultrasonic beams to scan in a sub-scanning direction (Z direction) perpendicular to the main scanning direction, thereby scanning the scanning region S that is a 3D space.

A transmitter/receiver 3 comprises a transmitter and a receiver. The transmitter portion of the transmitter/receiver 3 supplies electrical signals to the ultrasonic probe 2 so as to cause the ultrasonic probe 2 to generate ultrasonic beams. In addition, the receiver portion of the transmitter/receiver 3 receives echo signals that have been received by the ultrasonic probe 2.

The transmitter portion of the transmitter/receiver 3 comprises a clock generation circuit, a transmission delay circuit, and a pulsar circuit (not shown). The clock generation circuit is a circuit that generates clock signals to determine the transmission timing or the transmission frequency of the ultrasonic signal. The transmission delay circuit is a circuit that executes the transmission focus by applying a delay when transmitting ultrasonic waves. The pulsar circuit, which houses pulsars as many as individual channels corresponding to each ultrasonic transducer, generates a driving pulse at a transmission timing that is delayed in order to supply the same to each ultrasonic transducer of the ultrasonic probe 2.

The transmitter portion of the transmitter/receiver 3 generates ultrasonic beams by supplying electrical signals to the ultrasonic probe 2 in accordance with control signals outputted from a controller 8. The control signals include information that indicates the scanning range of the ultrasonic probe 2, and the transmitter drives the ultrasonic probe 2 in accordance with the information.

In addition, the receiver portion of the transmitter/receiver 3 comprises a preamplifier circuit, an A/D conversion circuit, and a reception delay/adder circuit (not shown). The preamplifier circuit amplifies, for each receiving channel, echo signals outputted from each ultrasonic transducer of the ultrasonic probe 2. The A/D conversion circuit provides A/D conversion of the amplified echo signals. The reception delay/adder circuit provides a delay time required to determine the receiving directivity of the echo signals after the A/D conversion for addition. With this addition, the reflected component in the direction of the receiving directivity is emphasized. Incidentally, the signals that have been added by the transmitter/receiver 3 are referred to as "RF data."

Under control by the controller 8, the transmitter portion of the transmitter/receiver 3 is capable of transmitting ultrasonic beams while partially thinning them out. In other words, the transmitter portion of the transmitter/receiver 3 is capable of transmitting ultrasonic beams by partially changing the scanning line density of the transmission thereof. In addition, the receiver portion of the transmitter/receiver 3 has a configuration capable of parallel signal processing under the control by the controller 8. In other words, the receiver portion of the transmitter/receiver 3 can generate a plurality of received beams corresponding to scanning lines in a plurality of different directions by a single transmission of ultrasonic beams. For example, when the number of parallel signal processings is "4," the transmitter/receiver 3 can generate received beams on four scanning lines that are symmetrically centered in the transmission direction by a single transmission of ultrasonic beams.

The transmitter/receiver 3 outputs the RF data to a signal processor 4. The signal processor 4 comprises a B-mode processor, a CFM processor, and the like.

The B-mode processor of the signal processor 4 converts the amplitude information of the echo to an image and generates ultrasonic raster data from the echo signals. Specifically, the B-mode processor executes band pass filter processing on the RF data, then detects the envelope line of the output signals, and applies compression processing to the detected data by means of logarithmic conversion. The signal processor 4 then outputs the ultrasonic raster data to an image-generating part 5.

In addition, the CFM processor of the signal processor 4 converts information regarding the moving bloodstream into an image and generates color ultrasonic raster data. The bloodstream information includes information regarding velocity, dispersion, power, and the like, and the bloodstream information is obtained as binarized information. Specifically, the CFM processing circuit is composed of a phase-detection circuit, an MTI filter, an autocorrelator, and a flow velocity/dispersion computing unit. This CFM processing circuit performs high-pass filter processing (MTI filter processing) for separating tissue signals and bloodstream signals, and determines the bloodstream information such as the moving velocity, dispersion, and power of the bloodstream for multipoint by means of the autocorrelation processing.

Upon receiving the plurality of ultrasonic raster data from the signal processor 4, the image-generating part 5 generates voxel data by means of coordinate conversion. The image-generating part 5 then generates ultrasonic-image data such as 3D image data and image data on an arbitrary cross section by applying image processing such as surface rendering processing, volume rendering processing, and MPR processing (Multi-Plannar Reconstruction) to the voxel data. The image-generating part 5 outputs the generated ultrasonic-image data to a display controller 7. Incidentally, this image-generating part 5 is equivalent to an example of the "image-generating part" of the present invention.

Figure 3A:
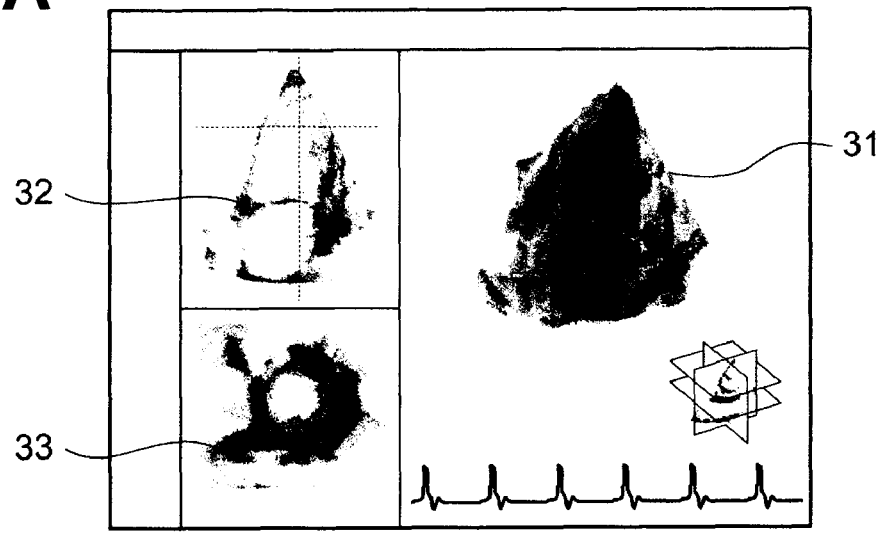
FIG. 3A is a diagram of a screen that shows an example of an ultrasonic image.
Figure 3B:
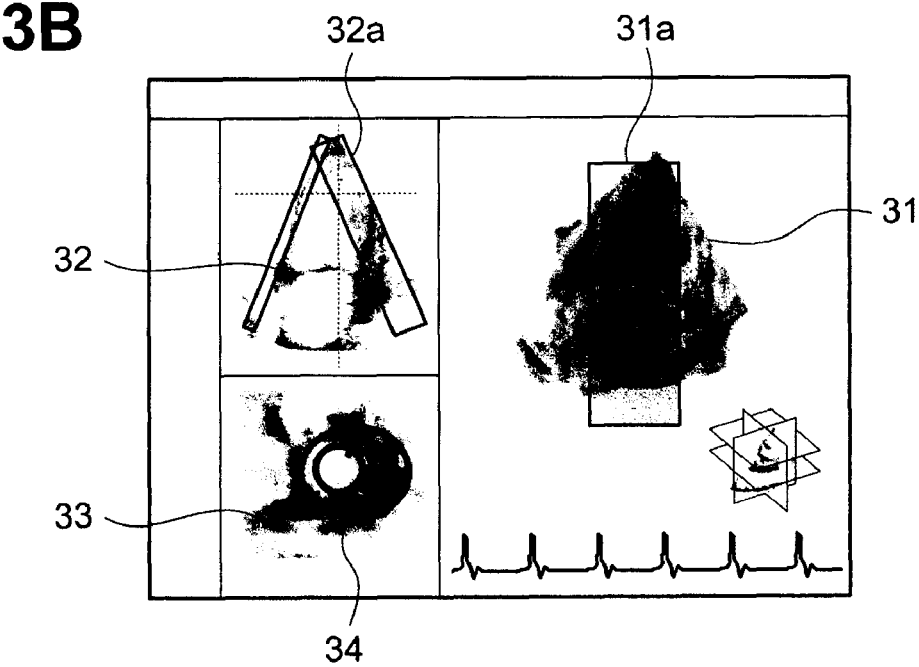
FIG. 3B is a diagram of a screen that shows an example of an ultrasonic image.

The display controller 6 instructs a display part 71 to display an image associated with the ultrasonic-image data generated by the image-generating part 5. Herein, an example of the image displayed on the display part 71 will be explained with reference to FIGS. 3A and 3B. FIGS. 3A and 3B are diagrams of a screen that shows an example of an ultrasonic image.

For example, the image-generating part 5 generates 3D image data, tomographic image data along a slice, and tomographic image data along a plane perpendicular to the transmission/reception direction of ultrasonic beams (hereinafter, referred to as "C plane image data"). Thereby, as shown in FIG. 3A, the display controller 6 instructs the display part 71 to display a 3D image 31, a tomographic image 32 along a slice, and a C plane image 33, simultaneously. Thus, displaying a plurality of types of images makes it possible to observe a diagnostic site from a plurality of directions. In FIG. 3A, a heart is considered as the diagnostic site by way of an example, and a 3D image, a tomographic image, and a C plane image of the heart are shown as an example. Incidentally, in the example shown in FIG. 3A, the tomographic image 32 along the slice represents a tomographic image along a long-axis view of a heart, and the C plane image 33 represents a tomographic image along a short-axis view of the heart.

The display controller 6 then generates a marker that indicates a region of interest (ROI) and instructs the display part 71 to display the marker, each overlapping each image. This region of interest (ROI) is a region for which the image quality is to be improved. For example, as shown in FIG. 3B, the display controller 6 generates a marker 34 that indicates the region of interest (ROI) and sends instructions to display marker 34 overlapping the C plane image 33. In addition, the display controller 6 instructs the display part 71 to display a marker 31a that represents the region of interest (ROI) in conformity with the position of marker 34, overlapping the 3D image 31. In other words, the display controller 6 generates marker 31a corresponding to marker 34 and instructs the display part 71 to display marker 31a overlapping the 3D image 31. Furthermore, the display controller 6 instructs the display part 71 to display marker 32a, which represents the region of interest (ROI), overlapping the tomographic image 32 in conformity with the position of marker 34. In other words, the display controller 6 generates marker 32a corresponding to marker 34 and instructs the display part 71 to display marker 32a overlapping the tomographic image 32. An operator can set a marker at an optional position by employing an input part 72, and can optionally change the shape of the marker. For example, when the operator designates an optional position by employing the input part 72, the display controller 6 sends instructions to display a marker at the designated position on the screen. The region of interest (ROI) that has been designated by the marker is a region from which a high-definition image is to be obtained.

In this embodiment, a heart is explained as the diagnostic site by way of an example. A heart wall of the heart is composed of three muscles (wall), and a coronary artery is situated in each muscle. When the motion of the coronary artery deteriorates, the cardiac function decreases and an infarction occurs. In this case, a high-definition ultrasonic image of the heart wall is necessary, because the diagnosis will be performed with a focus on the heart wall. To this end, the heart wall is included in the region of interest (ROI).

For example, a heart muscle is represented on the C plane image 33 which is along the short-axis view, so a region of interest (ROI) with a shape simulating the heart muscle is set on the C plane image 33. In the example shown in FIG. 3B, the display controller 6 generates a marker 34 simulating the shape of the heart muscle and sends instructions to display marker 34 overlapping the C plane image 33.

Figure 4:
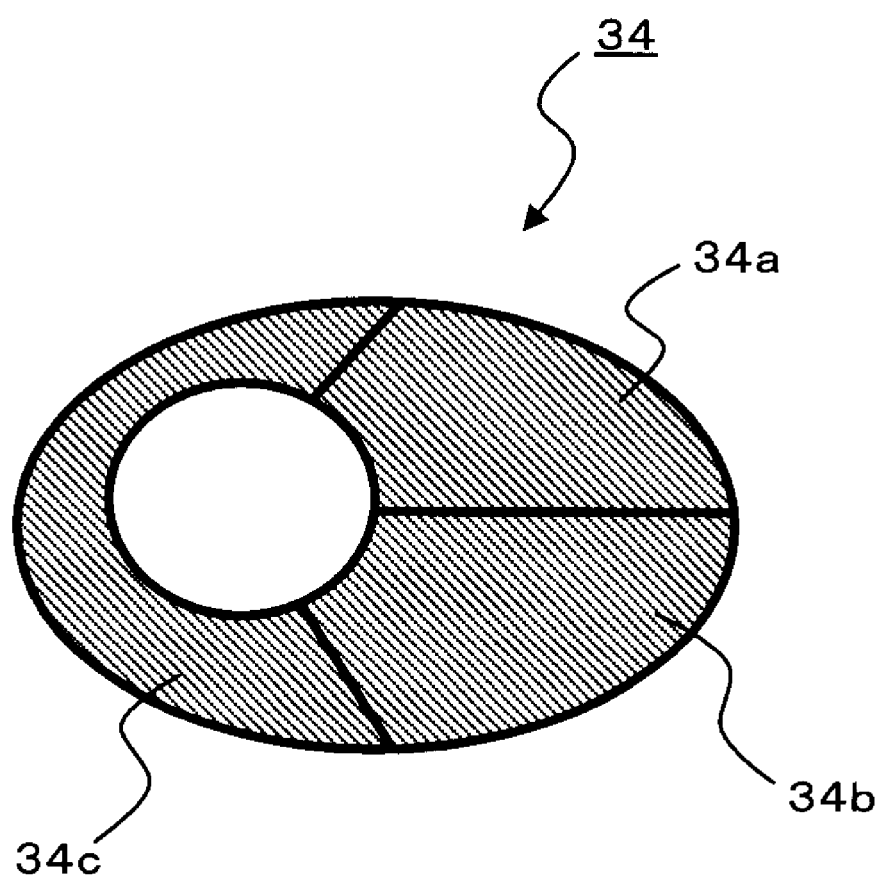
FIG. 4 is a diagram that shows an example of a typical marker representing a region of interest (ROI).

Herein, marker 34, which is displayed on the C plane image 33 and simulates the shape of the heart muscle, will be explained with reference to FIG. 4. FIG. 4 is a diagram that shows a typical example of a marker representing a region of interest (ROI).

As shown in FIG. 4, marker 34 simulating the shape of the heart muscle comprises two ellipses that are different in size. Specifically, the display controller 6 generates marker 34, which has an ellipse having a predetermined size and another ellipse having a larger size surrounding the ellipse.

Incidentally, marker 34 may comprise two circles that are different in size. In this case, marker 34 is configured so as to comprise a circle having a predetermined size and another circle having a larger size surrounding the circle.

The display controller 6 then divides marker 34 into three regions 34a, 34b, and 34c. The shapes of these three regions 34a, 34b, and 34c correspond to the shapes of three muscles (wall) in a heart wall on the short-axis view. This marker 34 has, for example, a shape according to the 16-segment method proposed by the American Society of Echocardiography (ASE).

The operator can change the shapes of these regions 34a, 34b, and 34c to an optional shape by using the input part 72. For example, when the operator designates a shape by using the input part 72, the display controller 6 changes the shapes of regions 34a, 34b, and 34c, depending on the designation and instructs display part 71 to display marker 34. Thus, displaying marker 34, which is equivalent to the shape of the heart wall, is displayed overlapping the C plane image 33 on which the heart muscle is represented, so as to facilitate setting of the region of interest (ROI) for the heart wall.

As described above, the region of interest (ROI) is designated using the marker simulating the shape of the site of interest, in order to allow the operator to easily designate a region from which he/she wants to obtain a high-definition image.

Furthermore, the operator may designate all regions among the three regions 34a, 34b, and 34c included in marker 34 as the region of interest (ROI) or may designate one or two regions among the three regions as the region of interest (ROI), by using the input part 72. For example, to observe all regions of the heart muscle in detail, the operator simply has to designate all of three regions 34a, 34b, and 34c included in marker 34 as the region of interest (ROI) by using the input part 72. Moreover, for example, to observe regions included in only region 34a in particular detail, the operator simply has to designate only region 34a as the region of interest (ROI) by using the input part 72.

Figure 5:
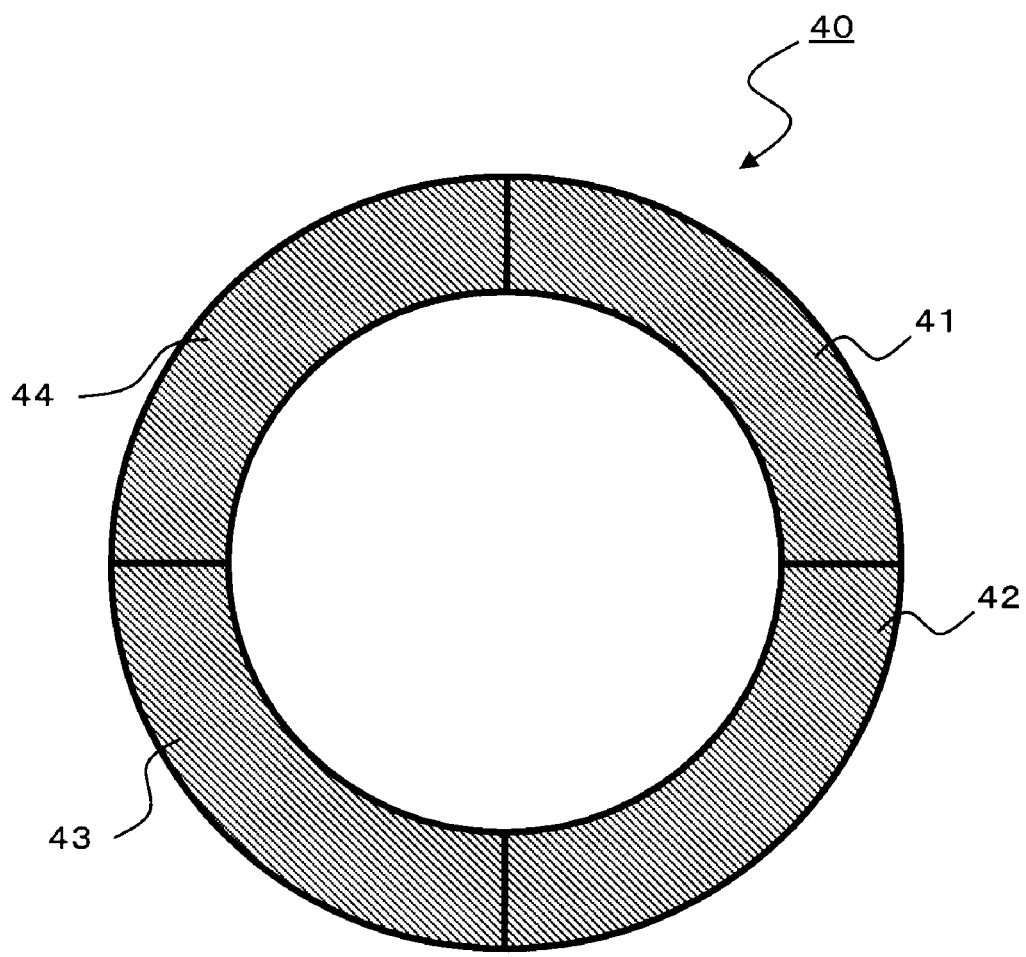
FIG. 5 is a diagram that shows an example of a typical marker representing a region of interest (ROI).

In addition, another example of a marker will be explained with reference to FIG. 5. FIG. 5 is a diagram that shows a typical example of a marker representing a region of interest (ROI).

As shown in FIG. 5, a marker 40 simulating the shape of the heart muscle comprises two ellipses or two circles that are different in size as is the case with marker 34 described above.

The display controller 6 divides the marker 40 into four regions 41, 42, 43, and 44. These four regions 41, 42, 43, and 44 correspond to the shapes of the heart wall on the short-axis view. This marker 40, for example, has a shape according to the 16-segment method proposed by the ASE.

For example, the shape of the region 41 corresponds to the shape of the anterior wall of a heart. In addition, the shape of the region 42 corresponds to the shape of the sidewall of the heart. Moreover, the shape of the region 43 corresponds to the shape of the lower wall of the heart. In addition, the shape of the region 44 corresponds to the shape of the septum of the heart. Thus, the marker 40, which is equivalent to the shape of the heart, is displayed overlapping the C plane image 33 on which the heart muscle is represented, so as to facilitate setting of the region of interest (ROI) for the heart wall.

Figure 6:
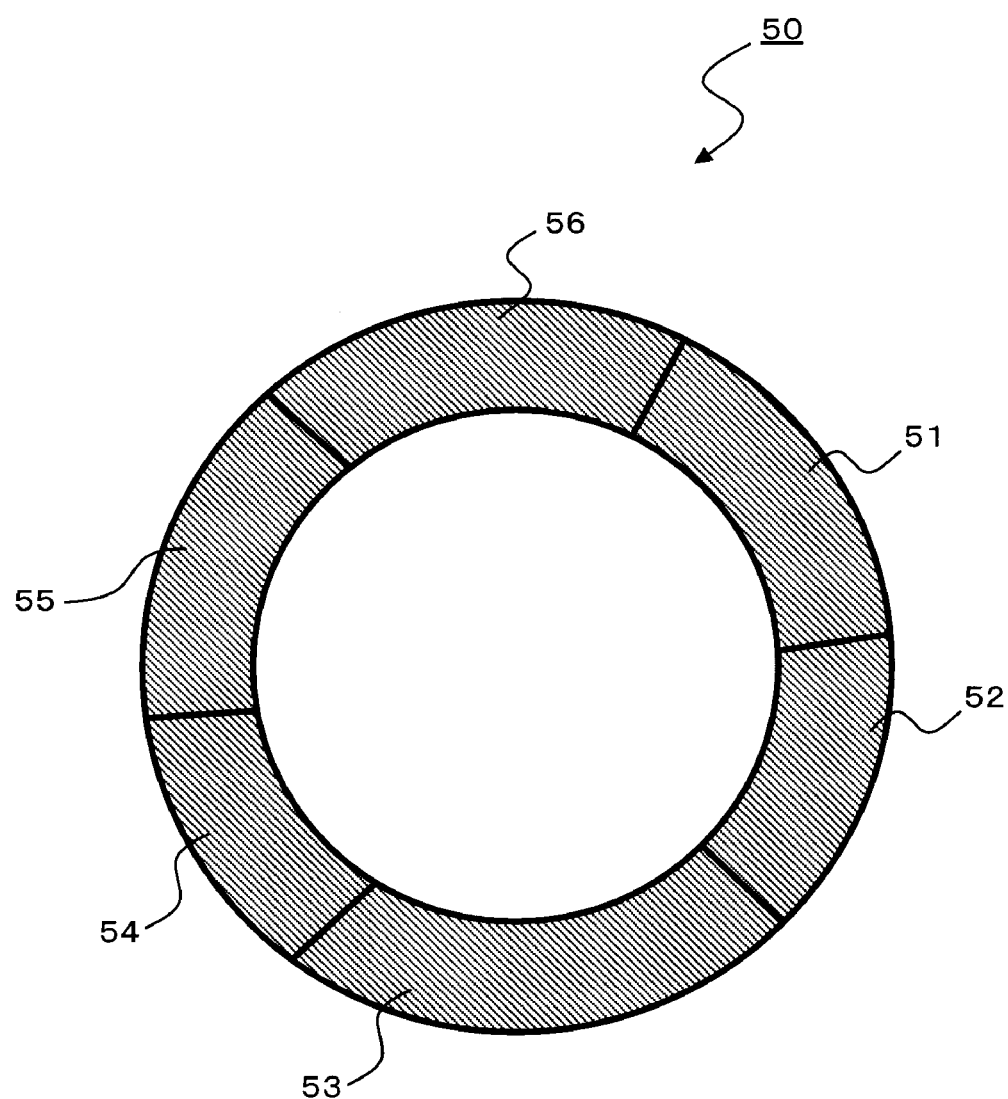
FIG. 6 is a diagram that shows an example of a typical marker representing a region of interest (ROI).

In addition, another example of a marker will be explained with reference to FIG. 6. FIG. 6 is a diagram that shows a typical example of a marker representing a region of interest (ROI).

As shown in FIG. 6, a marker 50 simulating the shape of a heart muscle comprises two ellipses or circles that are different in size as is the case with marker 34 described above.

The display controller 6 divides marker 50 into six regions 51 through 56. These six regions 51 through 56 correspond to shapes of the heart wall on the short-axis view. This marker 50 has, for example, a shape according to the 16-segment method proposed by the ASE.

For example, the shape of region 51 corresponds to the shape of the anterior wall of a heart. In addition, the shape of region 52 corresponds to the shape of the sidewall of the heart. Moreover, the shape of region 53 corresponds to the shape of the posterior wall of the heart. In addition, the shape of region 54 corresponds to the shape of the lower wall of the heart. Moreover, the shape of region 55 corresponds to the shape of the septum of the heart. In addition, the shape of region 56 corresponds to the shape of the anterior septum of the heart.

Thus, marker 50, which is equivalent to the shape of the heart, is displayed overlapping the C plane image 33 on which the heart muscle is represented, so as to facilitate setting of the region of interest (ROI) for the heart wall.

The operator can select a desired marker. For example, the display controller 6 instructs the display part 71 to display markers 34, 40, and 50 shown in FIGS. 4 through 6. The operator then selects the desired marker from markers 34, 40, and 50 by using the input part 72. The display controller 6 then instructs the display part 71 to display the marker that has been designated by the operator, overlapping the C plane image 33.

As described above, to follow the 16-segment method proposed by the ASE, a marker which is divided into three, four, or six regions is displayed overlapping the C plane image 33.

In this embodiment, a heart is explained as an example of the diagnostic site. For imaging a diagnostic site other than the heart, it is necessary to superimpose a marker simulating the shape of the diagnostic site over the image and to designate a region of interest (ROI) by means of the marker.

As described above, when the region of interest (ROI) is designated via a user interface 7, positional information (coordinate information) of the region of interest (ROI) is outputted from the user interface (UI) 7 to the controller 8.

The controller 8 controls each portion of the ultrasonic imaging apparatus 1. In this embodiment, the controller 8 receives the designation of the region of interest (ROI) from the user interface (UI) 7, and determines the number of transmission times of ultrasonic beams (scanning line density of the transmission) and the number of parallel signals. The controller 8 then controls the number of transmission times of ultrasonic beams (scanning line density of the transmission) of the transmitter portion of the transmitter/receiver 3, and further controls the number of parallel signals of the receiver portion of the transmitter/receiver 3.

Figure 7:
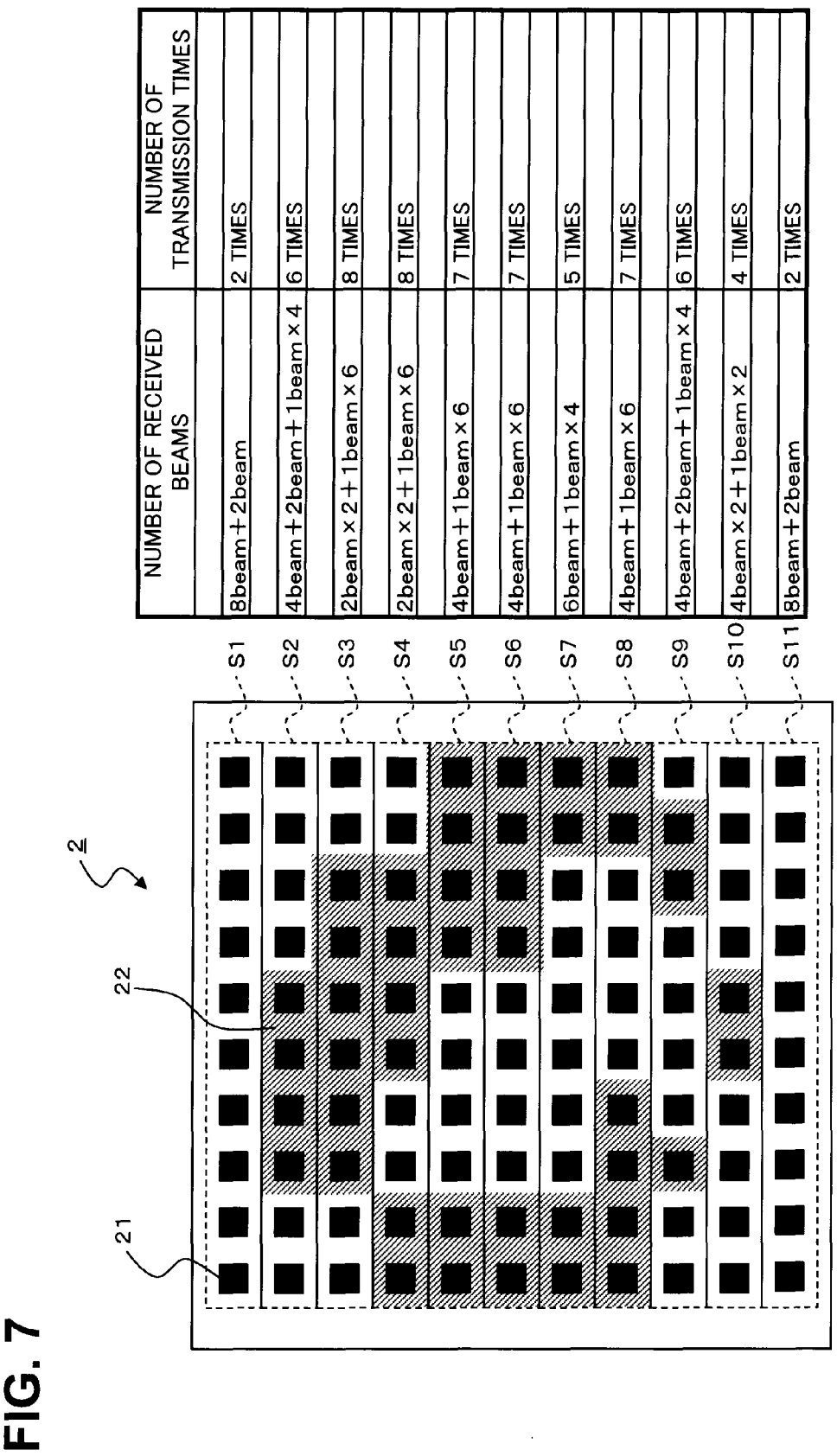
FIG. 7 is a diagram that shows the typical number of transmission times of ultrasonic beams and the number of received beams, respectively inside and outside the region of interest.

Specifically, the controller 8 comprises a scan-sequence-determining part 9 and a storage part 10. The scan-sequence-determining part 9 then determines the number of transmission times (scanning line density of the transmission) and the number of parallel signals, of ultrasonic beams. Hereinafter, the details of processing by the scan-sequence-determining part 9 are explained with reference to FIG. 7. FIG. 7 is a diagram that shows the number of transmission times and the number of received beams, of ultrasonic beams inside and outside the region of interest typically.

FIG. 7 is a pattern diagram of the ultrasonic probe 2 viewed from the upper portion. FIG. 7 represents a position for receiving ultrasonic beams 21, slices S1, S2, S3, . . . , and a region of interest (ROI) 22. The region of interest (ROI) 22 shaded in FIG. 7 is a region that has been designated by marker 34 shown in FIGS. 3B and 4. For example, when all regions among regions 34a, 34b, and 34c included in marker 34 are designated as the region of interest (ROI), the region of interest (ROI) 22 shown in FIG. 7 represents designated regions 34a, 34b, and 34c. Alternatively, when only region 34a included in marker 34 is designated, the region of interest (ROI) 22 shown in FIG. 7 represents region 34a.

In this embodiment, for the region of interest (ROI), the scanning line density of the transmission of the ultrasonic beams are increased in order to transmit ultrasonic beams. Conversely, for regions other than the region of interest (ROI), the ultrasonic beams are thinned out and transmitted, in order to reduce the number of transmission times of ultrasonic beams for parallel signal processing. This enables acquisition of a high-definition ultrasonic image for the region of interest (ROI). In addition, it is possible to improve the volume rate, because the number of transmission times of ultrasonic beams reduces in regions other than the region of interest (ROI). Therefore, it is possible to obtain the high-definition ultrasonic image in the region of interest (ROI) while preventing a decrease in the volume rate overall. In this embodiment, the maximum number of the number of parallel signals is "8" as an example. In other words, the transmitter/receiver 3 would be capable of generating received beams on up to eight scanning lines by a single transmission of ultrasonic beams.

For example, as shown in FIG. 3B, when the region of interest (ROI) is designated on the C plane image 33 via marker 34, positional information of marker 34 is outputted from the user interface (UI) 7 to the controller 8. Upon receiving the positional information of marker 34, the scan-sequence-determining part 9 determines, the number of transmission times of ultrasonic beams (scanning line density of the transmission) to the region of interest (ROI). This determination depends on the size of the region of interest (ROI) specified by marker 34 At this time, the scan-sequence-determining part 9 determines, for individual slices shown in FIG. 2B, the number of transmission times of ultrasonic beams to the region of interest (ROI). Furthermore, the scan-sequence-determining part 9 determines the number of transmission times of ultrasonic beams (scanning line density of the transmission) to regions other than the region of interest (ROI) and the number of parallel signals. At this time, the scan-sequence-determining part 9 determines, for individual slices shown in FIG. 2B, the number of transmission times of ultrasonic beams to regions other than the region of interest (ROI) and the number of parallel signals.

In addition, the scan-sequence-determining part 9 adjusts the number of transmission times of ultrasonic beams and the number of parallel signals per slice so that the numbers of received beams per slice are identical. For example, assume that the number of scanning lines per slice is ten. In this case, the scan-sequence-determining part 9 adjusts the number of transmission times of ultrasonic beams and the number of parallel signals per slice so that the total number of received beams per slice is ten.

A specific example of the number of transmission times of ultrasonic beams (scanning line density of the transmission) and the number of parallel signals that are set for each slice will be explained with reference to FIG. 7.

As shown in FIG. 7, the region of interest (ROI) 22 is not included in the slice S1, so the number of transmission times of ultrasonic beams to the slice S1 is reduced by performing parallel signal processing. For example, the scan-sequence-determining part 9 divides ten scanning lines included in the slice S1 into the range in which the number of parallel signals is "8" and the range in which the number of parallel signals is "2," and determines the number of transmission times of ultrasonic beams to be twice. Thereby, the transmitter portion of the transmitter/receiver 3 transmits ultrasonic beams twice to the slice S1. The receiver portion of the transmitter/receiver 3 generates eight received beams by a single transmission, and generates two received beams by another transmission. Therefore, the total number of received beams that are generated by two transmissions is "10."

In addition, the region of interest (ROI) 22 is included in the slice S2, so the scanning line density of ultrasonic beams is raised for regions included in the region of interest (ROI) 22. Conversely, for regions other than the region of interest (ROI), the number of transmission times of ultrasonic beams is reduced by performing parallel signal processing. For example, for regions included in the region of interest (ROI) 22 among ten scanning lines included in the slice S2, the scan-sequence-determining part 9 determines the number of transmission times of ultrasonic beams to be four times, depending on the size of the region. In addition, for regions other than the region of interest (ROI) 22, the scan-sequence-determining part 9 divides them into the range in which the number of parallel signals is "4" and the range in which the number of parallel signals is "2," and determines the number of transmission times of ultrasonic beams to be twice. In other words, the total of the numbers of transmission times of ultrasonic beams is six times for the slice S2. Thereby, the transmitter portion of the transmitter/receiver 3 transmits ultrasonic beams six times to the slice S2. Specifically, the transmitter portion of the transmitter/receiver 3 transmits ultrasonic beams four times to regions included in the region of interest (ROI) 22. The receiver portion of the transmitter/receiver 3 then generates four received beams in total. In addition, the transmitter portion of the transmitter/receiver 3 transmits ultrasonic beams twice to regions other than the region of interest (ROI) 22. The receiver portion of the transmitter/receiver 3 then generates four received beams by one transmission and generates two received beams by another transmission. Therefore, the total number of received beams that are generated by six transmissions is "10."

Moreover, the slice S3 includes the region of interest (ROI) 22, so scanning line density of ultrasonic beams is raised for regions included in the region of interest (ROI) 22. Conversely, for regions other than the region of interest (ROI) 22, the number of transmission times of ultrasonic beams is reduced by performing parallel signal processing. For example, for regions included in the region of interest (ROI) 22 among ten scanning lines included in the slice S3, the scan-sequence-determining part 9 determines the number of transmission times of ultrasonic beams to be six times, depending on the size of the region. In addition, for regions other than the region of interest (ROI) 22, the scan-sequence-determining part 9 divides them into the range in which the number of parallel signals is "2" and the range in which the number of parallel signals is "2," and determines the number of transmission times of ultrasonic beams to be twice. In other words, the total of the numbers of transmission times of ultrasonic beams is eight times for the slice S3. Thereby, the transmitter portion of the transmitter/receiver 3 transmits ultrasonic beams eight times to the slice S3. Specifically, the transmitter portion of the transmitter/receiver 3 transmits ultrasonic beams six times to regions included in the region of interest (ROI) 22. The receiver portion of the transmitter/receiver 3 then generates six received beams in total. In addition, the transmitter portion of the transmitter/receiver 3 transmits ultrasonic beams twice to regions other than the region of interest (ROI) 22. The receiver portion of the transmitter/receiver 3 then generates two received beams by a single transmission and generates two received beams by another transmission. Therefore, the total number of received beams that are generated by eight transmissions is "10."

Also for slices S4, S5, S6, . . . , regions included in the region of interest (ROI) 22 are scanned by raising the scanning line density of the transmission of ultrasonic beams. Conversely, for regions other than the region of interest (ROI) 22, the number of transmission times of ultrasonic beams is reduced by performing parallel signal processing.

As described above, the transmitter/receiver 3 raises the scanning line density of the transmission of ultrasonic beams for the region of interest (ROI) 22 and generates one received beam per transmission. Conversely, for regions other than the region of interest (ROI) 22, the transmitter/receiver 3 lowers the scanning line density of ultrasonic beams by performing parallel signal processing. Furthermore, it adjusts the number of transmission times of ultrasonic beams and the number of parallel signals so that the numbers of received beams on all slices are identical. In this embodiment, the scan-sequence-determining part 9 adjusts the number of transmission times of ultrasonic beams and the number of parallel signals in regions other than the region of interest (ROI) 22 so that the number of received beams per slice is ten.

The controller 8 then outputs the number of transmission times of ultrasonic beams per slice, the number of parallel signals, and the positional information of the region of interest (ROI) to the transmitter/receiver 3 by involving them in scanning conditions. Upon receiving the scanning conditions from the controller 8, the transmitter/receiver 3 scans, in accordance with the scanning conditions, the scanning region S shown in FIG. 2A using ultrasonic beams.

In addition, when the numbers of received beams per slice are not identical, the scan-sequence-determining part 9 may make the numbers of received beams per slice identical by changing the shape of the region of interest (ROI).

According to this embodiment, for the region of interest (ROI), it is possible to obtain a high-definition ultrasonic image by raising the scanning line density of the transmission of ultrasonic beams. In addition, for regions other than the region of interest (ROI), it is possible to improve the volume rate by reducing the number of transmission times of ultrasonic beams by performing parallel signal processing. This enables acquisition of a high-definition ultrasonic image for the region of interest (ROI) while preventing a decrease in the volume rate overall, resulting in maintaining real-time properties.

For example, when observing a heart muscle of a heart, with the ultrasonic imaging apparatus 1 according to this embodiment, it is possible to obtain a fine ultrasonic image of the heart muscle that is a site of interest while maintaining real-time properties to an extent that corresponds to the motion of the heart.

Furthermore, according to this embodiment, the numbers of received beams per slice are identical. This makes image processing easier, because it is not necessary to apply interpolation processing on the received beams that have been generated per slice. When the numbers of received beams per slice differ, it is necessary to generate voxel data by interpolating the received beams that have been generated for each slice. Conversely, in this embodiment, interpolation is not necessary, so image processing becomes easier to that extent. Consequently, it becomes possible to reduce the period that is required to generate ultrasonic-image data.

Incidentally, it is not necessary to adjust the number of transmission times of ultrasonic beams and the number of parallel signals so that the numbers of received beams per slice are identical. Then, for the region of interest (ROI), a scan is performed by raising the scanning line density of the transmission of ultrasonic beams. For regions other than the region of interest (ROI), the scanning line density of the transmission is lowered by performing parallel signal processing. In the region of interest (ROI), the scanning line density of the transmission of ultrasonic beams is higher, so a high-quality image can be obtained. In addition, in regions other than the region of interest (ROI), the number of transmission times of ultrasonic beams is reduced by parallel signals processing to make it possible to prevent a decrease in the volume rate. In this case, the image-generating part 5 is required to generate voxel data by interpolating the received beams that have been generated for each slice.

In addition, the storage part 10 stores a control program for controlling the operations of each part of the ultrasonic imaging apparatus 1. The control program includes a scan-sequence-determining program for executing the functions of the scan-sequence-determining part 9. The controller 8 comprises a CPU. When the CPU receives designation of a region of interest (ROI), the scan-sequence-determining program stored in the storage part 10 is executed, thereby determining the number of transmission times of ultrasonic beams per slice and the number of parallel signals. Incidentally, the ultrasonic probe 2, the transmitter/receiver 3, and the controller 8 are collectively equivalent to one example of the "scanner" of the present invention.

The user interface 7 comprises a display part 71 and an input part 72. The display part 71 is composed of a monitor such as a CRT and a liquid crystal display. An image such as a tomographic image, a 3D image, or bloodstream information is displayed on the screen of the display part 71. The input part 72 is composed of a pointing device such as a joystick or a trackball, a switch, buttons, a keyboard, a TCS (Touch Command Screen), or the like. Various settings such as scanning conditions, the region of interest (ROI), and the like are then inputted using the input part 72. The scanning conditions inputted by the input part 72 are transmitted to the controller 8.

Operation

Figure 8:
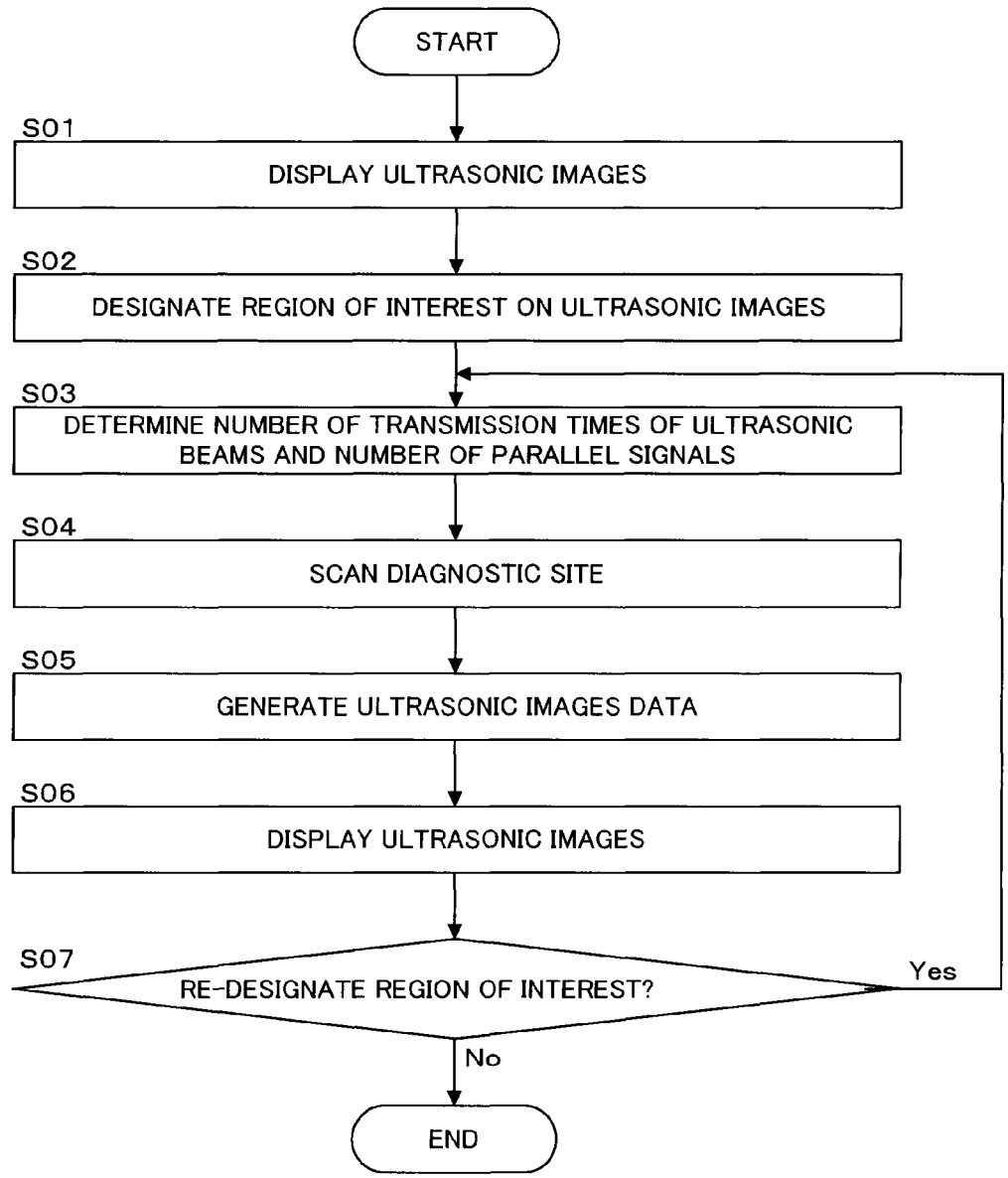
FIG. 8 is a flowchart that shows a series of operations by an ultrasonic imaging apparatus according to an embodiment of the present invention.

Next, the operations of the ultrasonic imaging apparatus according to an embodiment of the present invention are explained with reference to FIG. 8.

Step S01

First, by applying the ultrasonic probe 2 to the body surface of a subject, a diagnostic site (heart) is scanned using ultrasonic beams. The image-generating part 5 then generates 3D image data by applying volume rendering processing to voxel data obtained by the scan. In addition, the image-generating part 5 generates tomographic image data of an arbitrary cross section by applying MPR processing to the voxel data. The display controller 6 then instructs the display part 71 to display ultrasonic images that are based on the ultrasonic-image data generated by the image-generating part 5. For example, as shown in FIG. 3A, the display controller 6 instructs the display part 71 to display a 3D image 31, a tomographic image 32, and a C plane image 33, simultaneously.

Step S02

The display controller 6 then instructs the display part 71 to display a marker for specifying the region of interest (ROI) overlapping the ultrasonic image. For example, as shown in FIG. 3B, the display controller 6 overlaps a marker 31a on the 3D image 31, overlaps a marker 32a on the tomographic image 32, overlaps a marker 34 on the C plane image 33 and instructs the display part 71 to display them. An operator observes the ultrasonic image displayed on the display part 71 and changes the shape or position of the marker via the input part 72, so as to designate a site of interest. Positional information of the region of interest (ROI) that has been designated via the marker is outputted from the user interface 7 to the controller 8.

Step S03

Upon receiving the positional information of the region of interest (ROI) from the user interface 7, the scan-sequence-determining part 9 determines, for each slice, the number of transmission times of ultrasonic beams (scanning line density of the transmission) and the number of parallel signals. At this time, the scan-sequence-determining part 9 determines, depending on the size of the region of interest (ROI), the number of transmission times of ultrasonic beams (scanning line density of the transmission) for regions included in the region of interest (ROI). Furthermore, the scan-sequence-determining part 9 determines the number of transmission times of ultrasonic beams and the number of parallel signals, for regions other than the region of interest (ROI). In addition, the scan-sequence-determining part 9 adjusts the number of transmission times of ultrasonic beams and the number of parallel signals so that the numbers of received beams generated per slice are identical.

Step S04

The controller 8 outputs, to the transmitter/receiver 3, the scanning conditions including the number of transmission times of ultrasonic beams and the number of parallel signals, for each slice. The controller 8 then controls transmission/reception of ultrasonic beams of the transmitter/receiver 3. The transmitter/receiver 3 scans, under control by the controller 8, the scanning region S shown in FIG. 2A using ultrasonic beams in accordance with the scanning conditions.

Step S05

When the transmitter/receiver 3 generates received beams per slice, a predetermined processing is applied to the received beams by the signal processor 4. The signals that have been processed by the signal processor 4 are outputted to the image-generating part 5. The image-generating part 5 then generates ultrasonic-image data such as 3D image data, tomographic image data, or C plane image data.

Step S06

The display controller 6 instructs the display part 71 to display an ultrasonic image that is based on the ultrasonic-image data generated by the image-generating part 5. When the image-generating part 5 generates 3D image data, the display controller 6 instructs the display part 71 to display a 3D image that is based on the 3D image data. In addition, when the image-generating part 5 generates C plane image data, the display controller 6 instructs the display part 71 to display a C plane image that is based on the C plane image data.

As described above, in the region of interest (ROI), a high-definition image can be obtained, because the scanning line density of the transmission of ultrasonic beams is higher. In addition, in regions other than the region of interest (ROI), the number of transmission times of ultrasonic beams is reduced by parallel signal processing to make it possible to prevent a decrease in the volume rate. Moreover, making the number of received beams generated per slice identical removes the necessity for interpolation, so there is an effect of making image processing easier.

Step S07

When the operator observes the image displayed on the display part 71 and changes the position or shape of the region of interest (ROI) via the input part 72 (step S07, Yes), positional information of the region of interest (ROI) is outputted from the user interface 7 to the controller 8. The scan-sequence-determining part 9 determines the number of transmission times of ultrasonic beams (scanning line density of the transmission) and the number of parallel signals again (step S03). A new ultrasonic image is then obtained by executing the processes of steps S03 through S06.

Modified Example 1

Next, Modified Example 1 of the abovementioned embodiment will be explained. In the abovementioned embodiment, the transmitter/receiver 3 transmits ultrasonic beams also to regions other than the region of interest (ROI). In this Modified Example 1, the transmitter/receiver 3 may not transmit ultrasonic beams to regions other than the region of interest (ROI). Thus, only the region of interest (ROI) is scanned using ultrasonic beams, so the number of transmission times of ultrasonic beams will be reduced. Consequently, a decrease in the volume rate is prevented, resulting in maintaining real-time properties. At this time, a high-definition image can be obtained by scanning the region of interest (ROI) by raising the scanning line density of the transmission of ultrasonic beams, as is the case with the abovementioned embodiment.

In addition, in regions to which ultrasonic beams are not transmitted (regions other than the region of interest), the image-generating part 5 generates voxel data by making the number of received beams per slice identical, assuming that received beams are present. The image-generating part 5 then applies image processing to the voxel data. This makes it possible to omit interpolation by the image-generating part 5.

Modified Example 2

Next, Modified Example 2 of the abovementioned embodiment will be explained. In Modified Example 2, only a site (e.g., heart wall) that exists in front of the screen is scanned at high resolution in conformity with the orientation of the 3D image that is displayed on the display part 71. The display controller 6 instructs the display part 71 to display the 3D image that has been obtained in advance. When the operator gives an instruction to rotate the 3D image via the input part 72, the display controller 6 then instructs the display part 71 to rotate and display the 3D image in accordance with the instruction for rotation. With a 3D image displayed on the display part 71, rotation-positional information of the 3D image is then outputted from the user interface 7 to the controller 8. The scan-sequence-determining part 9 determines, based on the rotation-positional information, the number of transmission times of ultrasonic beams (scanning line density of the transmission) to the region, depending on the size of the region in front of the screen. At this time, the scan-sequence-determining part 9 determines, for individual slices shown in FIG. 2B, the number of transmission times of ultrasonic beams to the region in front of the screen. Furthermore, the scan-sequence-determining part 9 determines the number of transmission times of ultrasonic beams and the number of parallel signals, to regions other than the region in front of the screen. Thus, in regions other than the region in front of the screen, parallel signal processing is performed to reduce the number of transmission times of ultrasonic beams.

According to this Modified Example 2, the scanning line density of the transmission of ultrasonic beams is higher in the region in front of the screen, so a high-definition ultrasonic image can be obtained for the region. In addition, for regions other than the region in front of the screen, reducing the number of transmission times of ultrasonic beams by performing parallel signal processing makes it possible to improve the volume rate. Consequently, it becomes possible to obtain a high-definition ultrasonic image for the region in front of the screen while preventing a decrease in the overall volume rate.

What is claimed is:

1. An ultrasonic imaging apparatus comprising:
    a scanner configured to scan a 3D region using ultrasonic beams, a scanning line density of transmission of ultrasonic beams for a region of interest among said 3D regions being higher than a scanning line density of ultrasonic beams for regions other than said region of interest among said 3D regions, and
    an image-generating part configured to generate ultrasonic-image data of said 3D region, based on a received beam that has been obtained by said scan, wherein
    said scanner is configured to perform parallel signal processing in the regions other than said region of interest, and said scanning by said scanner comprises:
scanning a predetermined slice by using ultrasonic beams to scan in a main scanning direction;
scanning said 3D regions by scanning a plurality of slices by using ultrasonic beams to scan in a direction perpendicular to said main scanning direction, and
equalizing a number of received beams to be received per slice by changing a number of transmission times of ultrasonic beams and a number of parallel signals per said slice.

2. The ultrasonic imaging apparatus according to claim 1, wherein
said scanner is configured to perform said scan by varying a number of parallel signals between said region of interest and said regions other than the region of interest.

3. The ultrasonic imaging apparatus according to claim 1, wherein
said scanner comprises
a transmitting part configured to thin out and transmit ultrasonic beams for said regions other than the region of interest on said each slice, and
a receiving part configured to perform parallel signal processing for said regions other than the region of interest.

4. The ultrasonic imaging apparatus according to claim 1, further comprising
a controller configured to instruct a display apparatus to display an ultrasonic image obtained in advance, the ultrasonic image being along a plane generally perpendicular to a transmission direction of ultrasonic beams; and configured to receive a designation of said region of interest on said ultrasonic image along said generally-perpendicular plane, wherein
said scanner is configured to perform said scan in accordance with the designation of said region of interest received by said controller.

5. The ultrasonic imaging apparatus according to claim 4, wherein
said controller is further configured to perform:
generating a marker used for designating said region of interest, the marker having a shape that simulates a site to be diagnosed;
instructing said display apparatus to display said marker overlapping the ultrasonic image that is along said generally-perpendicular plane; and
receiving the designation of said region of interest via said marker.

6. The ultrasonic imaging apparatus according to claim 5, wherein
said controller is further configured to perform:
instructing said display apparatus to display an ultrasonic image based on ultrasonic-image data that is along said generally-perpendicular plane;
generating a marker for designating said region of interest, the marker simulating the shape of a heart, being divided into a plurality of regions, and being elliptical;
instructing said display apparatus to display said elliptical marker overlapping the ultrasonic image that is along said generally-perpendicular plane; and
receiving the designation of said region of interest via said elliptical marker.

7. The ultrasonic imaging apparatus according to claim 6, wherein
said controller is configured to generate said elliptical marker that has an ellipse having a predetermined size and another ellipse surrounding said ellipse to be displayed on said display apparatus.

8. The ultrasonic imaging apparatus according to claim 6, wherein
said controller is configured to generate said elliptical marker that is divided into three, four, or six regions to be displayed on said display apparatus.

9. The ultrasonic imaging apparatus according to claim 1, further comprising
a controller configured to instruct a display apparatus to display a 3D image obtained in advance, wherein
said scanner is configured to scan said 3D region using ultrasonic beams, said region of interest being a region that exists in front of a display screen of said display apparatus, a scanning line density of transmission of ultrasonic beams for said region of interest being higher than a scanning line density of transmission of ultrasonic beams for regions other than said region of interest.

10. A method of obtaining an ultrasonic image comprising
scanning a 3D region using ultrasonic beams, a scanning line density of transmission of ultrasonic beams for a region of interest among 3D regions being higher than a scanning line density of transmission of ultrasonic beams for regions other than said region of interest among said 3D regions, and
generating ultrasonic-image data of said 3D region, based on received beams that have been obtained by said scan, wherein
said scanning is performed by parallel signal processing in regions other than said region of interest, and
said scanning further comprises:
scanning a predetermined slice by scanning using said ultrasonic beams in a main scanning direction;
scanning said 3D regions by scanning a plurality of slices by using ultrasonic beams to scan in a direction perpendicular to the main scanning direction; and
equalizing a number of received beams to be received per slice by changing a number of transmission times of ultrasonic beams and a number of parallel signals per said slice.

11. The method of obtaining an ultrasonic image according to claim 10, wherein said scanning is performed by varying a number of parallel signals between said region of interest and said regions other than the region of interest.

12. The method of obtaining an ultrasonic image according to claim 10, wherein said scanning is performed by thinning out and transmitting ultrasonic beams to said regions other than the region of interest on said each slice, and by performing parallel signal processing in said regions other than the region of interest.

13. The method of obtaining an ultrasonic image according to claim 10, comprising:
displaying, before the scan, an ultrasonic image on a display apparatus that is along a plane generally perpendicular to a transmission direction of ultrasonic beams; and
performing said scan when said region of interest is designated on an ultrasonic image that is along said generally-perpendicular plane.

14. The method of obtaining an ultrasonic image according to claim 13, comprising
displaying, before the scan, a marker used for designating said region of interest, the marker having a shape that simulates a site to be diagnosed on display apparatus overlapping the ultrasonic image that is along said generally-perpendicular plane; and
performing said scan when said region of interest is designated via said marker.

15. The method of obtaining an ultrasonic image according to claim 14, wherein said marker is an elliptical marker that simulates a shape of a heart and is divided into a plurality of regions.

* * * * *